United States Patent
Dosho

(10) Patent No.: US 7,471,766 B2
(45) Date of Patent: Dec. 30, 2008

(54) X-RAY DIFFRACTION APPARATUS

(75) Inventor: Akihide Dosho, Tokyo (JP)

(73) Assignee: Rigaku Corporation, Akishima-Shi, Tokyo (JP)

(*) Notice: Subject to any disclaimer, the term of this patent is extended or adjusted under 35 U.S.C. 154(b) by 2 days.

(21) Appl. No.: 11/882,279

(22) Filed: Jul. 31, 2007

(65) Prior Publication Data
US 2008/0031416 A1 Feb. 7, 2008

(30) Foreign Application Priority Data
Aug. 1, 2006 (JP) .............................. 2006-210396

(51) Int. Cl.
*G01N 23/20* (2006.01)
(52) U.S. Cl. .......................................... 378/71; 378/73
(58) Field of Classification Search .............. 378/70–90
See application file for complete search history.

(56) References Cited

U.S. PATENT DOCUMENTS
3,852,594 A 12/1974 Paolini

FOREIGN PATENT DOCUMENTS

| JP | 53-28222 | 8/1978 |
|----|----------|--------|
| JP | 3-55890 | 12/1991 |
| JP | 2000-55837 A | 2/2000 |

*Primary Examiner*—Jurie Yun
(74) *Attorney, Agent, or Firm*—Buchanan Ingersoll & Rooney PC

(57) ABSTRACT

Disclosed is an X-ray apparatus having an X-ray source, an X-ray detector, a divergence slit, and a scattering slit. The incident angle $\theta$ of X-ray to be irradiated on a sample is changed at a predetermined angular speed at measurement time and diffracted X-ray detection angle $2\theta$ at which the X-ray detector detects X-ray is changed in the opposite direction to the $\theta$-direction at an angular speed double that of the X-ray incident angle $\theta$. The slit width of the divergence slit is changed such that the X-ray irradiation width always coincides with the sample width while the slit width of the scattering slit is retained at a constant value. The width of X-ray received by the X-ray detector is restricted by the narrower one of the divergence slit and the scattering slit. The resolution in the high angle region can be kept at a high level.

6 Claims, 12 Drawing Sheets

LOW ANGLE

BOUNDARY

HIGH ANGLE

LOW ANGLE
(PRIOR ART)

BOUNDARY
(PRIOR ART)

HIGH ANGLE
(PRIOR ART)

LOW ANGLE
(PRIOR ART)

BOUNDARY
(PRIOR ART)

HIGH ANGLE
(PRIOR ART)

X-RAY DIFFRACTION APPARATUS

BACKGROUND OF THE INVENTION

1. Field of the Invention

The present invention relates to an X-ray diffraction apparatus that restricts X-ray on the incident side by a divergence slit and restricts X-ray on the receiving side by a scattering slit.

2. Description of the Related Art

There is widely known an X-ray diffraction apparatus for analyzing the crystal structure of a substance. Some X-ray diffraction apparatus are based on the principle of a focusing method. This principle is sometimes called "Bragg-Brentano focusing method". As an X-ray diffraction apparatus using a focusing optical system, an apparatus shown in FIG. 7 is known. In this apparatus, an X-ray source F, a sample S, and a receiving slit RS are mounted on a focusing circle $C_f$. X-ray generated from the X-ray source F is incident on the sample S while its divergence is restricted by a divergence slit DS. When the diffraction condition of Bragg is satisfied, X-ray is diffracted by the sample S, and diffracted X-ray is passed through a scattering slit SS, focused on the focusing circle $C_f$ at the point of the receiving slit RS, and received by an X-ray detector DT.

The divergence slit DS mainly restricts X-ray so that X-ray emitted from the X-ray source F is irradiated on a predetermined area of the sample S. The receiving slit RS mainly prevents extra X-ray (other than X-ray focused on the focusing circle $C_f$) from being received by the X-ray detector DT. The scattering slit SS mainly prevents X-ray generated from a region other than the sample S (e.g., scattered X-ray generated due to air scattering) from being received by the X-ray detector DT.

There has been known the X-ray diffraction apparatus using a focusing optical system, such as those based on a fixed-divergence angle method and a constant-irradiation width method. In the fixed-divergence angle method as shown in FIG. 7, X-ray diffraction measurement is performed in a state where the slit widths of both the divergence slit DS and scattering slit SS of FIG. 7 are retained constant. FIGS. 8A to 8C concretely explain the fixed divergence angle method. FIG. 8A shows a state where the fixed-divergence angle method is used to measure a low angle region, FIG. 8C shows a state where a high angle region is measured, and FIG. 8B shows a boundary state between the states of FIGS. 8A and 8C.

The boundary state refers to a state where the X-ray width on the sample S defined by the slit width of the divergence slit DS and that of the scattering slit SS coincides with a sample width $W_s$ (e.g., $W_s$=20 mm) of the sample S when the diffraction angle 2θ is set to a predetermined value (e.g., 2θ=20°). This boundary state occurs under the condition (e.g., slit width d=1° or (½)° in terms of divergence angle, and sample width $W_s$=20 mm) generally applied to the focusing optical system.

As can be understood from FIGS. 8A to 8C, the slit width d of the divergence slit DS and slit width d of the scattering slit SS are retained at a constant value $d=d_0$ while X-ray incident angle θ changes from a low angle region ($<θ_1$) to high angle region ($>θ_1$). Thus, according to the fixed divergence angle method, the slit width d of the divergence slit DS is always retained at a constant value $d_0$, so that the amount of X-ray supplied to the sample S is kept constant even when the X-ray incident angle θ changes. As a result, the measurement that needs to be performed under the condition that the amount of X-ray is kept constant, such as a quantitative analysis, can be performed with high reliability. However, in the measurement of the low angle region shown in FIG. 8A, the area that is wider than the sample width of the sample S is irradiated with X-ray, so that not only diffracted X-ray from the sample S, but also diffracted or scattered X-ray from a sample holder 101 is generated. Accordingly, the background level in the measurement result is increased to lower the P/B ratio (Peak-to-Background ratio).

The constant-irradiation width method is a method that measures X-ray diffraction while changing the slit widths of both the divergence slit DS and scattering slit SS of FIG. 7. FIGS. 9A to 9C concretely explain the constant-irradiation width method. FIG. 9A shows a state where the constant-irradiation width method is used to measure the low angle region, FIG. 9C shows a state where the high angle region is measured, and FIG. 9B shows a boundary state between the states of FIGS. 9A and 9C. The definition of the boundary state is the same as that described in the above fixed-divergence angle method.

As can be understood from FIGS. 9A to 9C, the slit width d of the divergence slit DS is controlled such that X-ray irradiation width $W_0$ coincides with sample width $W_s$ while X-ray incident angle θ changes from a low angle region ($<θ_1$) to high angle region ($>θ_1$). At the same time, the slit width d of the scattering slit SS is controlled such that the corresponding X-ray width $W_0$ coincides with the sample width $W_s$. Thus, according to the constant-irradiation width method, the X-ray width on the sample S formed by the slits DS and SS always coincides with the sample width $W_s$. This prevents the area outside the sample S from being irradiated with X-ray even when the X-ray incident angle θ changes, thereby reducing the background to a lower level. Further, it is possible to increase the intensity of the diffracted X-ray in the high angle region by widening the X-ray irradiation angle. Thus, the constant-irradiation width method is mainly used in a qualitative analysis.

However, although the intensity of the diffracted X-ray is increased in the high angle region, resolution is decreased due to widening of the X-ray irradiation field. Further, the divergence slit width changes with a change of the X-ray incident angle θ and, accordingly, the amount of X-ray that has passed through the slit changes with the change of the X-ray incident angle θ with the result that the amount of X-ray irradiated on the sample S changes. Thus, the measurement that needs to be performed under the condition that the amount of X-ray is kept constant, (such as refined analysis, in general), cannot be performed with high reliability.

There is disclosed, in e.g., Japanese Patent Publication No. 53-28222 (FIG. 2, page 2), an X-ray diffraction apparatus having a configuration in which the slit width of the divergence slit on the incident side is made to change with a change of the X-ray incident angle while the scattering slit is not provided on the receiving side (i.e., the slit width of the scattering slit is fully opened). In this X-ray diffraction apparatus, the slit width of the divergence slit on the incident side changes with a change of the X-ray incident angle θ to thereby prevent the area outside the sample S from being irradiated with X-ray, eliminating the problem that the background level is increased. However, absence of the scattering slit on the receiving side may increase the background level.

Further, there is disclosed, in e.g., Japanese Utility Model Publication No. 3-55890 (FIG. 1, pages 1 to 2), a technique that changes the slit width of the divergence slit on the incident side with a change of the X-ray incident angle θ to thereby retain the X-ray irradiation width on the sample surface constant irrespective of the change of the X-ray incident angle. However, the above publication does not mention whether the scattering slit on the receiving side is provided or not and how to set the slit width of the scattering slit, if provided.

Further, there is disclosed, in e.g., Japanese Patent application Laid-Open Publication No. 2000-55837 (FIG. 1, Page 3), a technique that changes the slit width of the divergence slit with a change of the X-ray incident angle θ within a predetermined X-ray incident angle $\theta_a$ to allow the X-ray irradiation width on the sample surface to coincide with the sample width, while keeps the slit width of the divergence slit when the X-ray incident angle exceeds the predetermined angle $\theta_a$. This technique intended to prevent the area outside the sample width from being irradiated with X-ray on the low angle side relative to $\theta_a$ so as to reduce the background level and to keep the slit width of the divergence slit on the high angle side relative to $\theta_a$ to prevent the X-ray irradiation field on the sample surface from being widened so as to obtain high resolution.

However, the X-ray diffraction apparatus according to the technique disclosed in Japanese Patent Application Laid-Open Publication No. 2000-55837 could not obtain desired high resolution on the high angle side. The present inventor made various experiments in order to find out the reason for this and, consequently, found out that the reason is that slit control is not made on the receiving side although the slit width of the divergence slit is controlled on the incident side. Although FIG. 2 of Japanese Patent Laid-Open Publication No. 2000-55837 shows a state where some kind of a slit member is provided on the receiving side, the slit member depicted there is a receiving slit used in a typical X-ray diffraction apparatus, not a slit member having a function of restricting the X-ray width on the sample surface. The present inventor did not intend to give a special function to the slit member on the receiving side at the time the application was filed.

Today, demand for an X-ray diffraction measurement is diversified. For example, there is not only a demand for a satisfactory P/B ratio in a low angle region with respect to the diffraction angle (2θ) but also for a high resolution in a high angle region with respect to the diffraction angle (2θ). Such a demand is particularly growing in the field of photocatalysis. A catalyst is generally a substance that speeds up a reaction, but is chemically unchanged itself during the reaction. A photocatalyst is one of those catalysts and a substance that shows the catalytic reaction when exposed to light. Recently, it was found that a slight difference in the crystal structure of $TiO_2$ (titania), which is used as a photocatalyst, leads to a large difference in its photocatalysis function. Thus, it becomes necessary to separate the peaks in a high angle region (e.g., region at which 2θ is set to about 70°) also for management of a production process. Accordingly, there is required an X-ray diffraction apparatus capable of separating $TiO_2$ mixture into respective crystal phases: Anatase (see FIG. 10), Rutile (see FIG. 11), and Brookite (see FIG. 12) and analyzing the component fraction thereof.

FIGS. 10 to 12 are diffraction profiles of respective crystal systems. The respective graphs show different peak values from each other at the region in the vicinity of 2θ=70°. By detecting these peak values, it is possible to determine respective crystal phases. Thus, in order to make this determination, there is a demand for an X-ray diffraction measurement capable of obtaining a high resolution at a high angle region including the region at which 2θ is set to about 70°.

However, the X-ray diffraction apparatuses disclosed in Japanese Patent Publication No. 53-28222, Japanese Utility Model Publication No. 3-55890, and Japanese Patent Laid-Open Publication No. 2000-55837 could not obtain a satisfactory resolution in the high angle region with respect to diffraction angle 2θ. According to the present inventor's consideration, it is assumed that the reason for this is that, in the X-ray diffraction apparatuses disclosed in Japanese Patent Publication No. 53-28222 and Japanese Utility Model Publication No. 3-55890, the amount of X-ray that is irradiated on a sample in the high angle region for controlling the slit width of the divergence slit on the incident side changes, and unnecessary scattered X-ray cannot be eliminated due to absence of the scattering slit on the receiving side.

Further, in the apparatus disclosed in Japanese Patent Laid-Open Publication No. 2000-55837, the slit width of the divergence slit is controlled in the low angle region while the slit width of the divergence slit is kept constant in the high angle region. Therefore, the apparatus was expected to retain a high resolution in the high angle region because the amount of X-ray is kept constant in the high angle region. Actually, however, it was impossible to perform measurement with a high resolution in the high angle region due to absence of the scattering slit for restricting the X-ray width on the sample on the receiving side.

Further, the apparatus disclosed in Japanese Patent Laid-Open Publication No. 2000-55837 adopts a technique that widens the slit width of the divergence slit on the low angle side relative to a predetermined X-ray incident angle $\theta_a$ while keeps the slit width of the divergence slit on the high angle side relative to the predetermined angle $\theta_a$, which complicates the slit width control of the divergence slit, resulting in an increase in cost.

SUMMARY OF THE INVENTION

The present invention has been made in view of the above problems, and an object thereof is to provide an X-ray diffraction apparatus capable of obtaining a high resolution in the high angle region with respect to diffraction angle 2θ and simplifying control of the slit width.

According to an aspect of the present invention, there is provided an X-ray diffraction apparatus including: an X-ray source which generates X-ray to be irradiated on a sample; an X-ray detector which detects X-ray emitted from the sample; a divergence slit which is disposed between the X-ray source and the sample, the slit width of which can be controlled; a scattering slit which is disposed between the sample and X-ray detector, the slit width of which is constant; a θ rotator which changes the incident angle (θ) of X-ray emitted from the X-ray source and entering the sample through the divergence slit; a 2θ rotator which changes the diffracted X-ray detection angle (2θ) at which the X-ray detector detects X-ray diffracted by the sample and passed through the scattering slit; and a divergence slit width controller which controls the slit width of the divergence slit, wherein the X-ray incident angle (θ) is changed by the θ rotator, the diffracted X-ray detection angle (2θ) is changed by the 2θ rotator such that the diffracted X-ray detection angle (2θ) at which the X-ray detector detects X-ray is kept at an angle double that of the X-ray incident angle (θ); the slit width of the divergence slit is controlled by the divergence slit width controller such that the irradiation width of X-ray to be irradiated on the sample is made constant during a change in the X-ray incident angle (θ), the slit width of the scattering slit is kept constant, and in this state, X-ray emitted from the sample is detected by the X-ray detector.

According to the X-ray diffraction apparatus of the present invention, the slit width of the divergence slit is controlled by the divergence slit width controller, thereby allowing the irradiation width of X-ray to be irradiated on the sample surface to always coincide with the sample width. As a result, it is possible to perform accurate measurement while reducing the background to a lower level.

Further, according to the X-ray diffraction apparatus of the present invention, the scattering slit having a constant slit width is provided on the receiving side, allowing the amount of X-ray received by the X-ray detector to be made constant by the scattering slit even if the slit width of the divergence slit provided on the incident side is changed to change the X-ray irradiation width on the sample surface. In the conventional X-ray diffraction apparatus having a configuration in which the slit width of the divergence slit on the incident side is controlled while the scattering slit having a constant slit width is not provided on the receiving side, or in the conventional X-ray diffraction apparatus having a configuration in which the slit widths of both the divergence slit on the incident side and scattering slit on the receiving side are made constant, a high resolution could not be obtained in the high angle region in the X-ray diffraction measurement. On the other hand, according to the X-ray diffraction apparatus of the present invention having a configuration in which the slit width of the divergence slit on the incident side is made changeable while the slit width of the scattering slit on the receiving side is retained constant, it is possible to selectively perform background removal which is brought about the control of the slit width of the divergence slit and maintenance of the amount of X-ray which is brought about the constant slit width according to the need, thereby performing high precision measurement. In particular, since X-ray diffraction measurement can be performed with a higher resolution in the high angle region, it is possible to perform highly accurate separation of the peak of a photocatalyst such as $TiO_2$ having different peaks corresponding to a difference in the crystal structure in the high angle region (that is, for example, a region at which $2\theta$=about 70°).

Further, with regard to the amount of X-ray received by the X-ray detector, the narrower one of the X-ray irradiation width on the sample surface which is defined by the divergence slit on the incident side and X-ray irradiation width on the sample surface which is defined by the scattering slit on the receiving side is effective. This prevents a portion (e.g., a sample holder) other than the sample from being irradiated with X-ray to allow the P/B ratio on the low angle side to be kept high. Further, since the intensity of the diffracted X-ray with respect to the sample in the present invention is equivalent to that in a typical fixed-divergence angle method (that is, the amount of diffracted X-ray can be kept constant regardless of diffraction angle $2\theta$), it is possible to obtain a proper intensity ratio concerning a plurality of peaks having different $2\theta$ value and to kept a high resolution in the high angle region.

Further, in the high angle region, the X-ray width can be restricted by the scattering slit on the receiving side, so that it is possible to perform measurement by continuously increasing, from a minimum value, the width of the divergence slit throughout the entire region from the low angle region to high angle region without changing a control mode for the slit width of the divergence slit in the way of the measurement, thereby simplifying the operation of the slit width control.

As described above, an example of the high angle region with respect to the diffraction angle $2\theta$ is a region at which $2\theta$=about 70°. The angle defining the boundary between the low angle region and high angle region can be considered as follows. In the present invention, the slit width of the scattering slit provided on the receiving side is kept constant, and it is preferable that the value of the slit width be determined based on in which angle region the sample to be measured has a peak. Specifically, it is preferable that the value of the slit width of the scattering slit be set so that the resolution can be increased within the wavelength region including the peak of the sample. For example, for a sample having a peak on the comparatively high angle side, the slit width is set to comparatively a large value (e.g., 1° or 2°). On the other hand, for a sample having a peak on the comparatively low angle side, the slit width is set to comparatively a small value (e.g., (⅙)° or (½)°).

When the slit width of the scattering slit is set to a predetermined value and the scattering slit having the slit width is rotated about the sample during measurement, the X-ray width (that is, X-ray width expected by the slit width) defined on the sample surface in correspondence with the slit width of the scattering slit is changed with the rotation of the scattering slit. Specifically, the smaller the rotation angle is, the wider the X-ray width on the sample surface becomes, and the X-ray width gradually becomes narrower as the rotation angle becomes larger (up to 90°).

The above-mentioned boundary angle between the low angle region and high angle region is an angle of the scattering slit relative to the sample obtained when the X-ray width defined on the sample surface by the set slit width of the scattering slit coincides with the sample width. For example, assuming that the set slit width is 1° and the sample width is 20 mm, the boundary angle becomes 20° (in terms of $2\theta$). Thus, the region smaller than 20° is defined as the low angle region and region larger than 20° is defined as the high angle region. As described above, the concrete definition of the angle range of the low angle region and the high angle region, is changed depending on the size of the slit width of the scattering slit and dimension of the goniometer radius of an X-ray optical system or the like.

The apparatus disclosed in Japanese Patent Laid-Open Publication No. 2000-55837 controls the slit width of the divergence slit such that the X-ray irradiation width on the sample always coincides with the sample width on the low angle side relative to the boundary diffraction angle $\theta_a$ and keeps the slit width of the divergence slit to a constant value on the high angle side relative to the angle $\theta_a$. That is, the slit control mode is changed at the boundary diffraction angle $\theta_a$. To change the control mode during measurement requires a complicated control circuit, causing an increase in production cost and maintenance cost.

On the other hand, according to the present invention, even when the slit width of the divergence slit is increased at a constant speed throughout the entire region from the low angle region (<$\theta_a$) to high angle region (>$\theta_a$) without changing the control mode for the slit width of the divergence slit at the boundary angle $\theta_a$, the resolution in the high angle region can be kept high by the function of the scattering slit having a constant slit width. The above control of the slit width of the divergence slit, that is, an increase of the slit width of the divergence slit at a constant speed throughout the entire region from the low angle region to high angle region can be realized by a very simple control circuit, thereby reducing production cost.

In the X-ray diffraction apparatus according to the present invention, it is preferable that the divergence slit controller control the slit width of the divergence slit such that the irradiation width of X-ray on the sample surface coincides with the sample width of the sample. This configuration prevents a portion other than the sample from being irradiated with X-ray. As a result, it is possible to obtain a measurement result in which the background is reduced to a lower level and thereby the peak is easily recognized. In this case, the above control of the slit width can be performed throughout the entire region from the low angle region to high angle region with respect to the diffraction angle.

In the X-ray diffraction apparatus according to the present invention, it is preferable that the slit width of the scattering slit on the receiving side be constant at the point where the divergence angle is $(½)°$, $1°$, or $2°$. By setting the slit width of the scattering slit to $1°$, the resolution in the angle area, in which the peak of a sample which is considered to have a peak in the comparatively high angle area, can be improved. By setting the slit width of the scattering slit to $2°$, the resolution in the angle area, in which the peak of a sample which is considered to have a peak in the further high angle area, can be improved. By setting the slit width of the scattering slit to $(½)°$, the resolution in the angle area, in which the peak of a sample which is considered to have a peak in the comparatively low angle area, can be improved.

In the X-ray diffraction apparatus according to the present invention, it is preferable that the slit width of the scattering slit be constant at the point where the divergence angle is $(½)°$, $1°$, or $2°$. Further, it is preferable that when the angle $(2\theta)$ of the scattering slit relative to X-ray entering the sample falls within a range of $10°$ to $40°$, the X-ray width on the sample which is defined by the slit width of the scattering slit coincide with the sample width of the sample.

In the case where the slit width of the scattering slit is $1°$ in terms of divergence angle, the X-ray width on the sample defined by the slit width of the scattering slit coincides with the sample width of the sample when the angle $(2\theta)$ of the scattering slit relative to X-ray entering the sample is $20°$. In the case where the slit width of the scattering slit is $(½)°$ in terms of divergence angle, the X-ray width on the sample defined by the slit width of the scattering slit coincides with the sample width of the sample when the angle $(2\theta)$ of the scattering slit relative to X-ray entering the sample is $10°$. When a main peak occurs in a region at which $2\theta>20°$, the slit width $1°$ is selected. When a main peak occurs in a region at which $2\theta>10°$, the slit width $(½)°$ is selected. This configuration is a favorable optical condition for a typical sample.

BRIEF DESCRIPTION OF THE DRAWINGS

FIGS. 2A to 2C are views each showing a state where measurement is performed using the apparatus of FIG. 1, in which FIG. 2A is a view showing a state where X-ray enters a sample at a low angle, FIG. 2B is a view showing a state where X-ray enters a sample at a boundary diffraction angle, and FIG. 2C is a view showing a state where X-ray enters a sample at a high angle;

FIGS. 8A to 8C are views showing a fixed-divergence angle method which is an example of a conventional X-ray diffraction measurement, in which FIG. 8A is a view showing a state where X-ray enters a sample at a low angle, FIG. 8B is a view showing a state where X-ray enters a sample at a boundary diffraction angle, and FIG. 8C is a view showing a state where X-ray enters a sample at a high angle;

FIGS. 9A to 9C are views showing a constant-irradiation width method which is an example of a conventional X-ray diffraction measurement, in which FIG. 9A is a view showing a state where X-ray enters a sample at a low angle, FIG. 9B is a view showing a state where X-ray enters a sample at a boundary diffraction angle, and FIG. 9C is a view showing a state where X-ray enters a sample at a high angle;

DETAILED DESCRIPTION OF THE PREFERRED EMBODIMENTS

Figure 1:
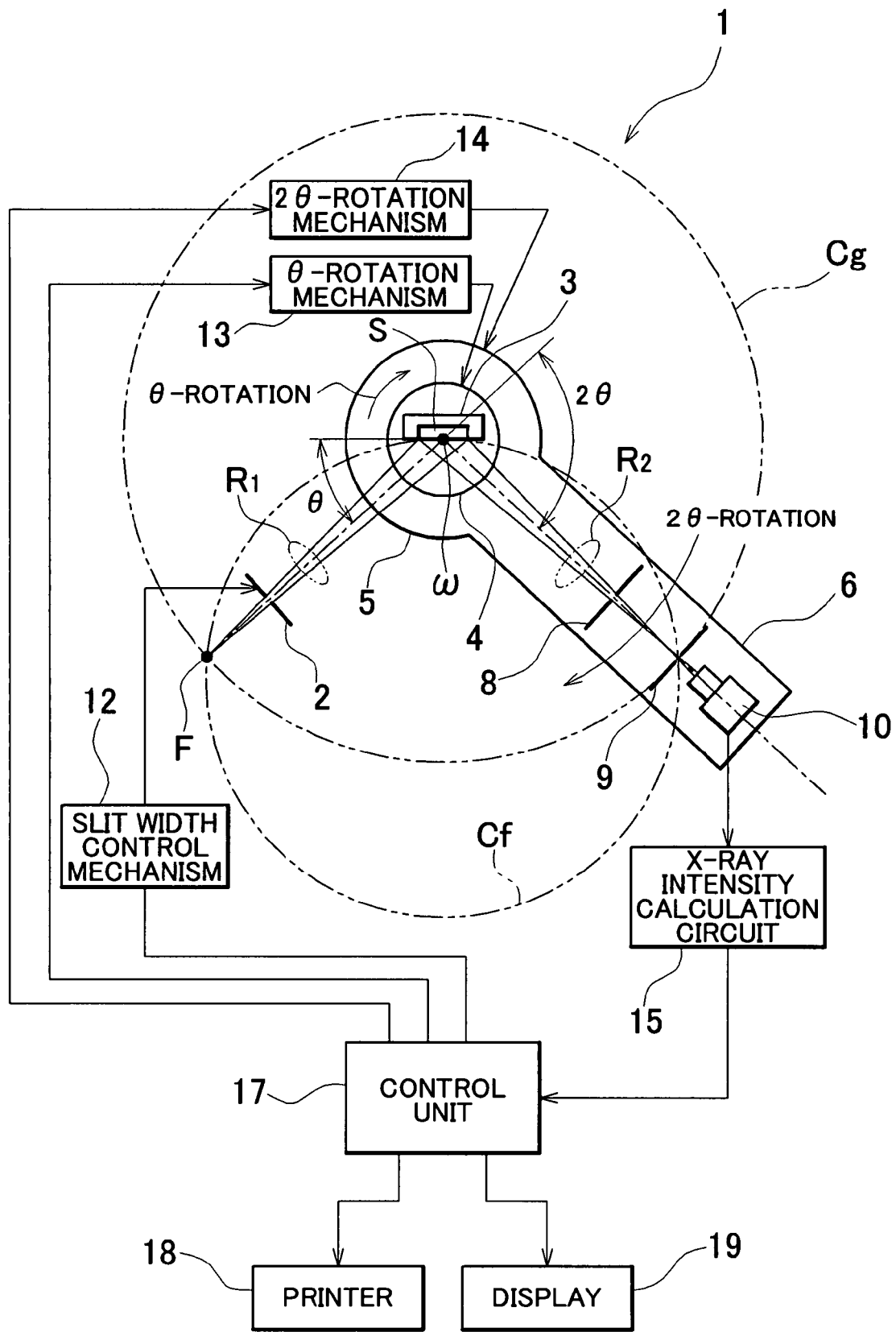
FIG. 1 is a plan view showing an embodiment of an X-ray diffraction apparatus according to the present invention.

An X-ray apparatus according to the present invention will be described based on a preferred embodiment. It should be noted that the present invention is not limited to the following embodiment. Although the following description is made with the accompanying drawings, there is a case where components in the drawings may be shown at a different scale from actual ones for easy understanding of their feature points.

FIG. 1 shows an embodiment of an X-ray diffraction apparatus according to the present invention. An X-ray diffraction apparatus 1 shown in FIG. 1 has an X-ray source F for generating X-ray, a divergence slit 2 for restricting divergence of X-ray, a $\theta$-rotation table 4 for supporting a sample holder 3, a $2\theta$-rotation table 5 coaxially arranged with the $\theta$-rotation table 4, and a detector arm 6 extending from the $2\theta$-rotation table 5. The X-ray source F and the divergence slit 2 are fixed so as not to be moved. A sample S which is an object to be measured is filled in a predetermined position of the sample holder 3. A scattering slit 8, a receiving slit 9, and an X-ray detector 10 are fixed on the detector arm 6.

A slit width control mechanism 12 is coupled to the divergence slit 2. The slit width control mechanism 12 controls the slit width of the divergence slit 2 to widen and narrow. The slit width control mechanism 12 may be constituted by, for example, a lead screw coupled with the output shaft of an electric motor and a slit member held in thread-engagement with the lead screw. A $\theta$-rotation mechanism 13 is coupled to the $\theta$-rotation table 4. A $2\theta$-rotation mechanism 14 is coupled to the $2\theta$-rotation table 5. The $\theta$-rotation mechanism 13 and $2\theta$-rotation mechanism 14 are mechanisms for rotating the $\theta$-rotation table 4 and $2\theta$-rotation table 5 with high angular accuracy. The above mechanisms may use a power transmission system including, e.g., a worm and a worm wheel to transmit rotation of an electric motor such as a servomotor and a pulse motor to the respective rotation tables 4 and 5.

The scattering slit 8 and the receiving slit 9 each have a constant slit width. The scattering slit 8 prevents scattered X-ray generated from a region other than the sample (e.g., scattered X-ray generated due to air scattering) from being received by the X-ray detector 10. The receiving slit 9 is disposed at a focal point of X-ray diffracted by the sample S and prevents X-ray other than the focused X-ray from being received by the X-ray detector 10. The slit width of the scattering slit 8 is $1°$ in terms of divergence angle. The slit width of the receiving angle 9 is 0.3 mm. The divergence angle 1° which represents the slit width of the scattering slit 8 is a slit width effective for a sample having a peak in the range not less than diffraction angle 20°. For a sample having a peak on a higher angle side, a scattering slit having a wider (e.g., divergence angle 2°, or 4°) slit width is used. On the other hand, for a sample having a peak on a lower angle side, a scattering slit having a narrower (e.g., divergence angle (½)°, or (⅙)°) slit width is used.

The X-ray detector 10 is, e.g., a zero-dimensional X-ray detector. The zero-dimensional X-ray detector detects a mass of X-ray received at a predetermined area without determining its reception position. The X-ray detector 10 outputs a signal corresponding to the amount of the received X-ray. Based on the output signal, an X-ray intensity calculation circuit 15 calculates the X-ray intensity.

The incident angle at which X-ray $R_1$ emitted from the X-ray source S enters the sample S through the divergence slit 2 is assumed to be "$\theta$". Further, the diffraction angle of diffracted X-ray $R_2$ detected by the X-ray detector 10 is assumed to be "$2\theta$". When the $\theta$-rotation table 4 is rotated by the $\theta$-rotation mechanism 13, the X-ray incident angle $\theta$ correspondingly changes. This rotation of the $\theta$-rotation table 4 is referred to as "$\theta$ rotation". When the $2\theta$-rotation table 5 is rotated by the $2\theta$-rotation mechanism 14, the diffraction angle $2\theta$ correspondingly changes. This rotation of the $2\theta$-rotation table 5 is referred to as "$2\theta$ rotation". The $2\theta$-rotation table is rotated ($2\theta$-rotated) at an angular speed double that of the $\theta$-rotation of the $\theta$-rotation table 4 in the same direction.

When the X-ray incident angle $\theta$ and X-ray diffraction angle $2\theta$ change, the X-ray source F and the receiving slit 9 move on a goniometer circle $C_g$ having a central axis $\omega$ passing along the surface of the sample S and extending horizontally in the paper plane in FIG. 1. When the X-ray incident angle $\theta$ and the X-ray diffraction angle $2\theta$ change, three points of the X-ray source F, the sample S, and the receiving slit 9 move on a focusing circle $C_f$.

The X-ray intensity signal output from the X-ray intensity calculation circuit 15 is input to a control unit 17. The control unit 17 is constituted by a computer including a CPU (Central Processing Unit), a memory, and the like. The slit width control mechanism 12, the $\theta$-rotation mechanism 13, and the $2\theta$-rotation mechanism 14 are connected to an output section of the control unit 17. Further, a printer 18 and a display 19 are connected to the output section of the control unit 17.

Operation of the X-ray diffraction apparatus having the configuration described above will be described.

Figure 2A:
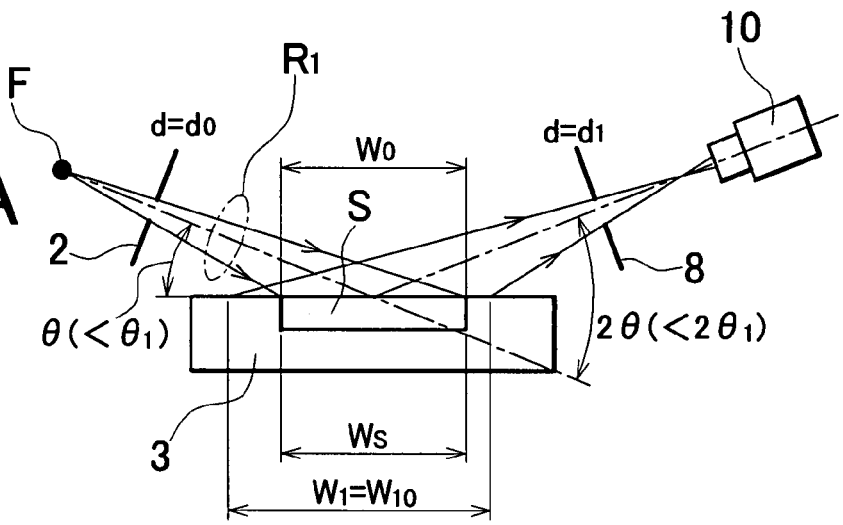
Figure 2B:
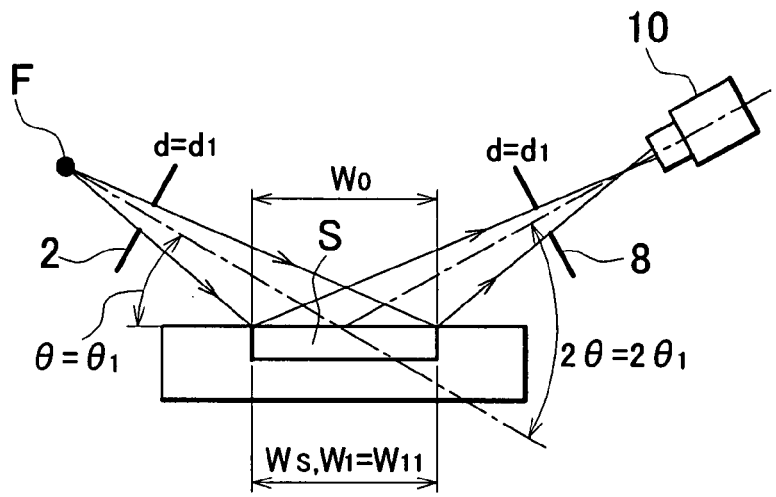
Figure 2C:
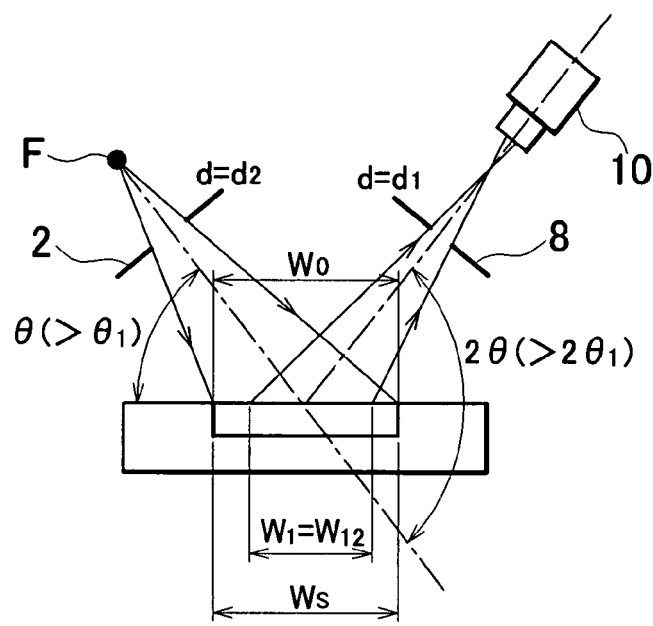

The X-ray incident angle $\theta$ is continuously changed for scanning at a predetermined angular speed or intermittently changed at a predetermined step angle from the low angle region ($<\theta_1$) shown in FIG. 2A to high angle region ($>\theta_1$) shown in FIG. 2C, depending on the characteristics of the sample S to be measured. That is, $\theta$-rotation is performed. At this time, diffracted X-ray detection angle $2\theta$ which is the rotation angle of the X-ray detector 10 is changed for scanning (that is, $2\theta$-rotation is performed) at an angular speed double that of $\theta$-rotation.

While the incident X-ray $R_1$ is $\theta$-rotated from the low angle region (FIG. 2A) to high angle region (FIG. 2C), the slit width of the divergence slit 2 is controlled by the slit width control mechanism 12 to be gradually moved (increased) from $d_0$ to $d_2$ according to the $\theta$-rotation. This movement is controlled such that X-ray irradiation width $W_0$ defined by the divergence slit 2 always coincides with sample width $W_s$.

On the other hand, while the X-ray incident angle $\theta$ is changed from the low angle region (FIG. 2A) to high angle region (FIG. 2C), that is, while the X-ray detector 10 is rotated from the low angle region (FIG. 2A) to high angle region (FIG. 2C), the slit width d of the scattering slit 8 is kept at a constant value $d_1$ (in the present embodiment, $d_1$ is set to 1°). Therefore, the X-ray width W1 defined on the sample surface by the scattering slit 8 is gradually narrowed from $W_{10}$ to $W_{12}$.

The state shown in FIG. 2B is a state where the diffraction angle $2\theta$ of the scattering slit 8 coincides with the $2\theta_1$ and X-ray width $W_1$ ($=W_{11}$) defined on the surface of the sample S by the slit width $d_1$ of the scattering slit 8 coincides with the sample width $W_s$. The sample width $W_s$ is set to 20 mm in a typical measurement, and diffraction angle $2\theta$ ($=2\theta_1$) at which the X-ray width $W_1$ corresponding to the scattering slit 8 having a slit width of 1° becomes 20 mm is 20°. Hereinafter, the diffraction angle $2\theta_1$ at which the X-ray width $W_1$ corresponding to the slit width d of the scattering slit 8 coincides with the sample width $W_s$ is referred to as "boundary diffraction angle".

The state shown in FIG. 2A where the diffraction angle $2\theta$ is smaller than the boundary diffraction angle $2\theta_1$ is a state of "low angle region". On the other hand, the state shown in FIG. 2C where the diffraction angle $2\theta$ is larger than the boundary diffraction angle $2\theta_1$ is a state of "high angle region". In the case of the low angle region (FIG. 2A), the X-ray width $W_{10}$ on the sample surface to be set by the slit width $d_1$ of the scattering slit 8 is larger than the sample width $W_s$. In the case of the high angle region (FIG. 2C), the X-ray width $W_{12}$ on the sample surface to be set by the slit width $d_1$ of the scattering slit 8 is smaller than the sample width $W_s$.

In FIGS. 2A to 2C, the X-ray incident angle $\theta$ is moved for scanning from the low angle region ($<\theta_1$) to high angle region ($>\theta_1$) while the surface of the sample S is scanned with X-ray and, correspondingly, X-ray detector 10 and scattering slit 8 are moved from the low angle region ($<2\theta_1$) to high angle region ($>2\theta_1$). Meanwhile, when the Bragg's diffraction condition: $2d \sin \theta = n\lambda$ (d: lattice spacing, $\lambda$: wavelength of X-ray, n: reflection order) is satisfied between the X-ray incident angle $\theta$ and sample S, X-ray diffraction occurs on the sample S. Then, the X-ray detector 10 detects the diffracted X-ray and outputs a detection signal. The output signal is transmitted to the X-ray intensity calculation circuit 15 shown in FIG. 1, and the X-ray intensity calculation circuit 15 calculates the X-ray intensity based on the received signal and transmits a result of the calculation to the control unit 17. The control unit 17 stores in a memory the X-ray intensity I as I($\theta$) in relation to the X-ray incident angle $\theta$.

Figure 3:
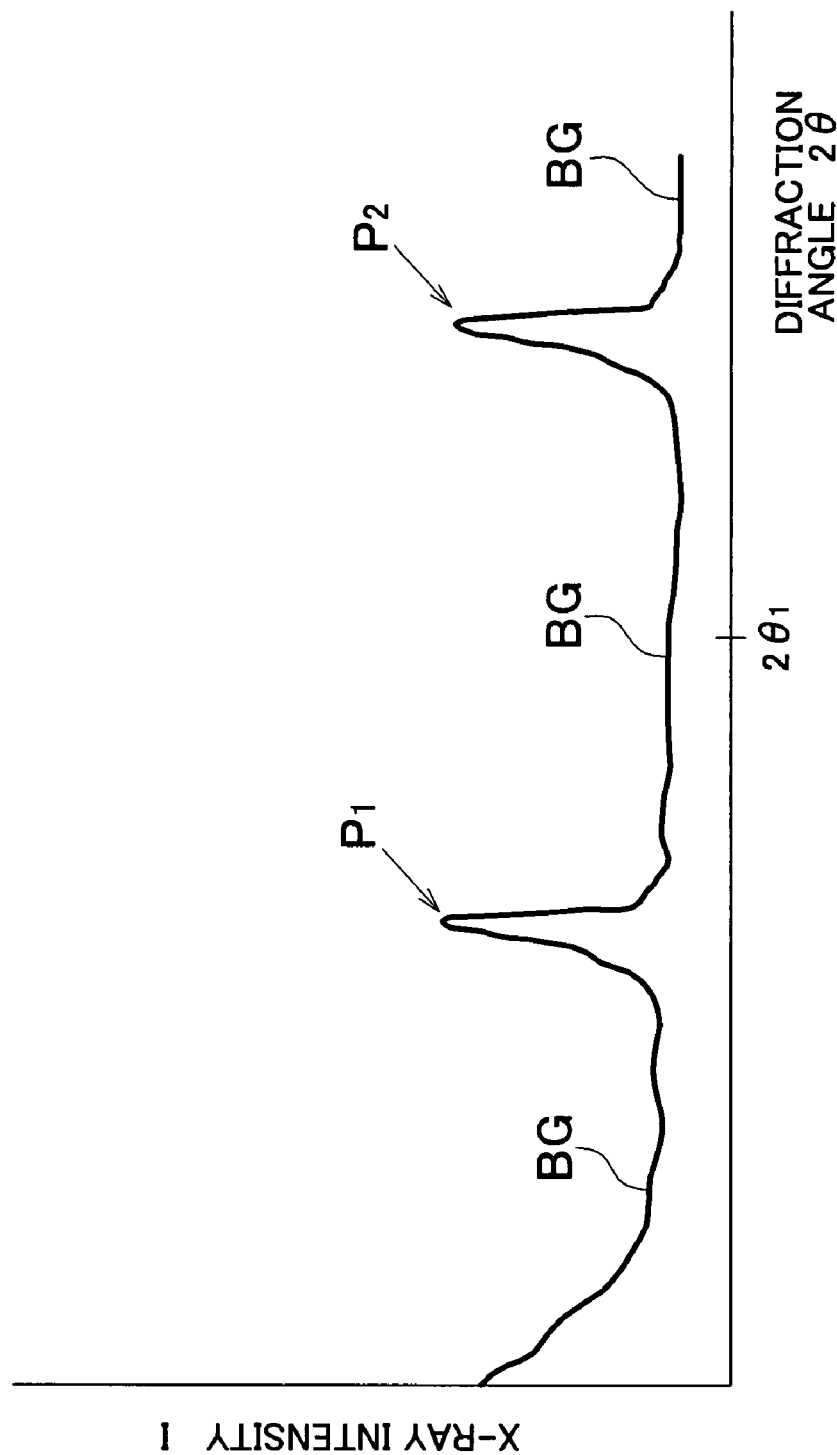
FIG. 3 is a graph showing an example of a result obtained by measurement performed using the apparatus of FIG. 1.

After completion of the measurement described above, or during the measurement, the control unit 17 outputs a measurement result to the printer 18 as printed information or displays the measurement result on the screen of the display 19 as image information. For example, as shown in FIG. 3, a profile in which peaks P1 and P2 corresponding to the diffracted X-ray appear relative to a background BG can be obtained.

As shown in FIGS. 2A to 2C, in the X-ray diffraction apparatus according to the present embodiment, the X-ray irradiation width $W_0$ on the incident side is controlled by the control unit 17 and slit width control mechanism 12 of FIG. 1 to always coincide with the sample width $W_s$ while the measurement is performed from the low angle region ($<2\theta_1$) (FIG. 2A) to high angle region ($>2\theta_1$) (FIG. 2C). That is, the X-ray irradiation width is controlled to be constant. On the other hand, on the receiving side, the slit width of the scattering slit 8 is fixed to a constant value (in the present embodiment, the slit width is fixed to 1° in terms of divergence angle).

The above configuration prevents the area other than the sample from being irradiated with the incident X-ray, thereby reducing the background to a lower level. Further, since the slit width of the scattering slit 8 on the receiving side is constant, even if the X-ray irradiation width with respect to the sample becomes wider in the measurement of the high angle region, the amount of the X-ray received by the X-ray detector 10 can be kept constant and, therefore, refined analysis can be achieved.

Japanese Patent Laid-Open Publication No. 2000-55837 discloses in FIG. 1 thereof a technique that controls the slit width of the divergence slit (4) on the low angle side relative to a boundary diffraction angle ($\theta_a$) to allow the X-ray irradiation width on the sample surface to coincide with the sample width, while keeps the slit width of the divergence slit to a constant value ($2\beta_a$) on the high angle side relative to the boundary angle ($\theta_a$). This technique intended to prevent the area outside the sample width from being irradiated with X-ray on the low angle side relative to $\theta_a$ so as to reduce the background level and to keep the slit width of the divergence slit on the high angle side relative to $\theta_a$ to prevent the X-ray irradiation field on the sample surface from being widened so as to obtain high resolution.

However, in the case where the control mode for the slit width of the divergence slit is changed at the boundary angle ($\theta_a$) as described above, it is difficult to manage the timing of the mode change in an accurate fashion. Further, the structure of a control circuit becomes complicated. As a result, production cost is increased. On the other hand, in the X-ray diffraction apparatus according to the present embodiment, as shown in FIGS. 2A to 2C, the slit width d of the divergence slit 2 on the incident side is simply controlled to be changed with a constant increase rate throughout the entire region from the low angle region (<$2\theta_1$) to high angle region (>$2\theta_1$). Thus, the control can easily be carried out.

In the case of the X-ray diffraction apparatus according to the present embodiment shown in FIGS. 2A to 2C, when the diffraction angle $2\theta$=about 10°, the slit width d of the divergence slit 2 becomes ($\frac{1}{2}$)°, and when diffraction angle $2\theta$=about 40°, the slit width d of the divergence slit 2 becomes 2°.

Next, an advantage of reducing the background in the low angle region to a lower level which is realized by the X-ray diffraction apparatus according to the present embodiment will be considered.

Figure 4:
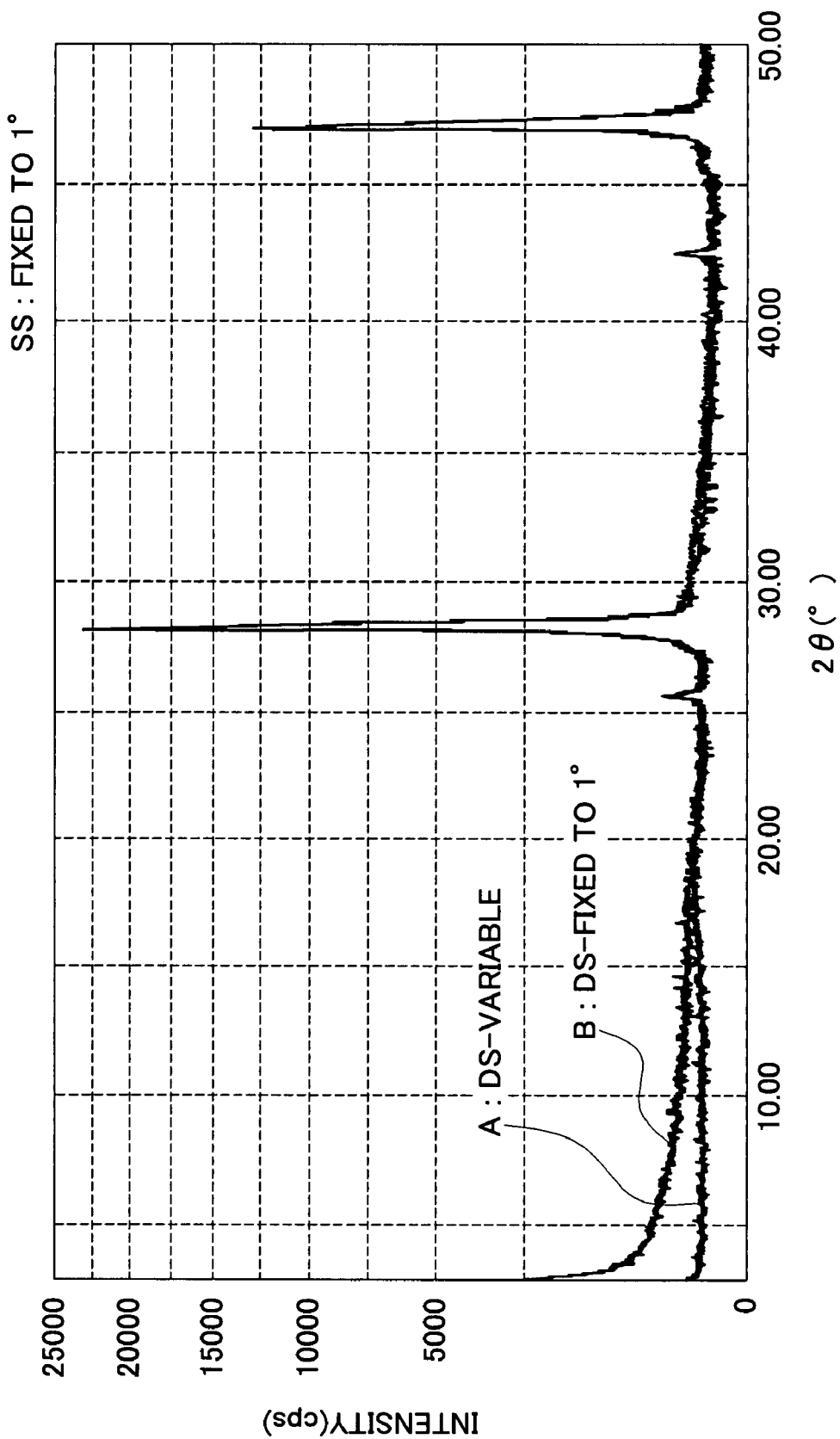
FIG. 4 is a graph for explaining an advantage of reducing the background in the low angle region to a lower level in the measurement performed using the apparatus of FIG. 1.

FIG. 4 shows an X-ray diffraction profiles of A (which is obtained in the case where a variable divergence slit is used) and B (which is obtained in the case where fixed (1°) divergence slit is used), in which the scattering slit is set to 1°. As can be understood from the graph, a significant difference appears in the background value between profiles A and B in the region in which $2\theta$ becomes less than 20°.

Figure 5:
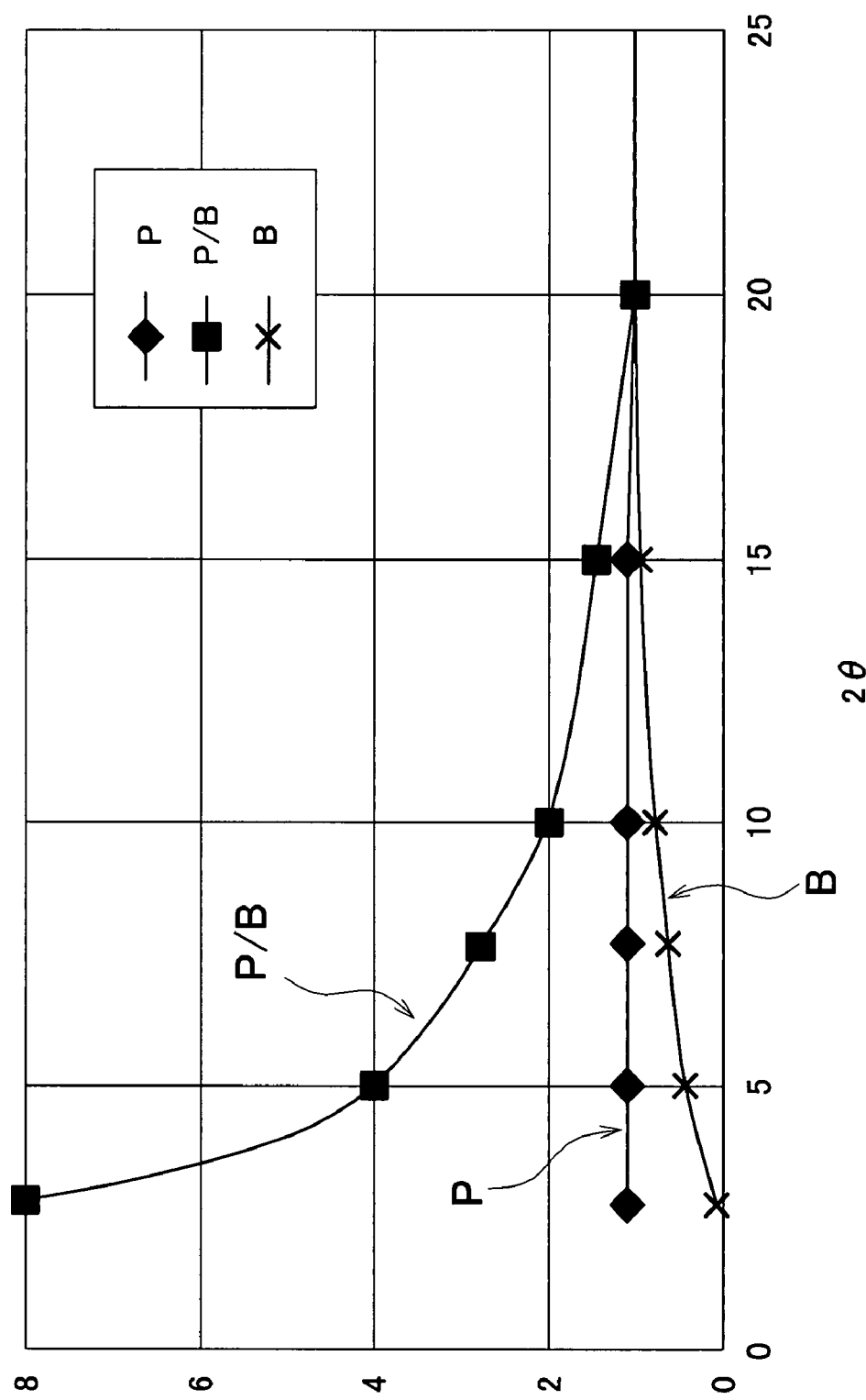
FIG. 5 is a graph showing that the background in the low angle region is reduced to a lower level in the measurement performed using the apparatus of FIG. 1.

FIG. 5 shows how the P/B ratio in the low angle region at which diffraction angle $2\theta$<20° is improved in the X-ray diffraction apparatus according to the present embodiment shown in FIGS. 1 and 2, as compared to the conventional fixed-divergence angle method. The fixed-divergence angle method is, as described above, a method that measures X-ray diffraction in a state where the slit widths of both the divergence slit on the incident side and the scattering slit on the receiving side are fixed to a constant value (e.g., divergence angle 1°).

In FIG. 5, a straight line P is a value obtained when the peak intensity in the conventional fixed divergence angle method is set as a denominator and peak value in the method according to the present invention is set as a numerator. As shown in FIG. 5, values of the peak intensity itself of the diffracted X-ray obtained by both the method according to the present embodiment and conventional fixed divergence angle method are entirely the same as each other. Therefore, the ratio of numerator/denominator becomes "1" and the straight line P is obtained.

Figure 8A:
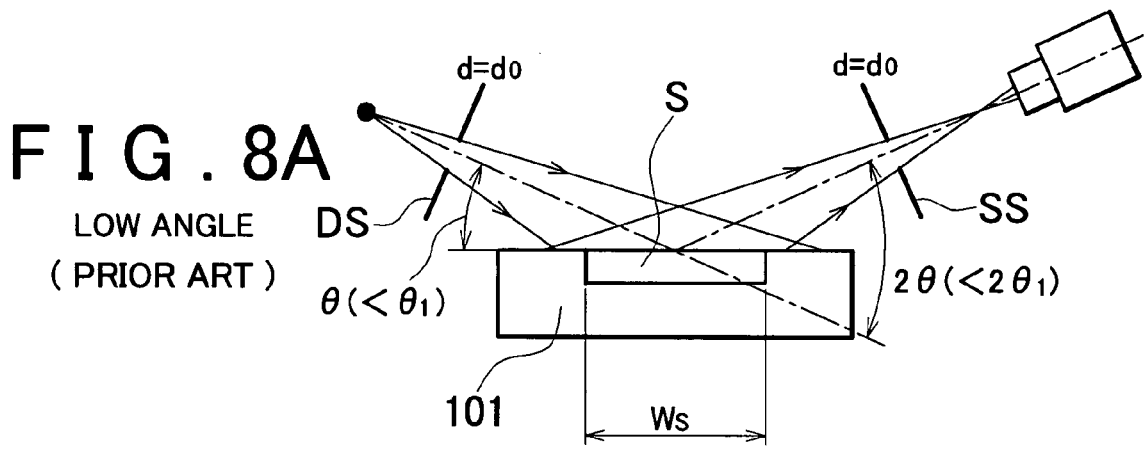
Figure 8B:
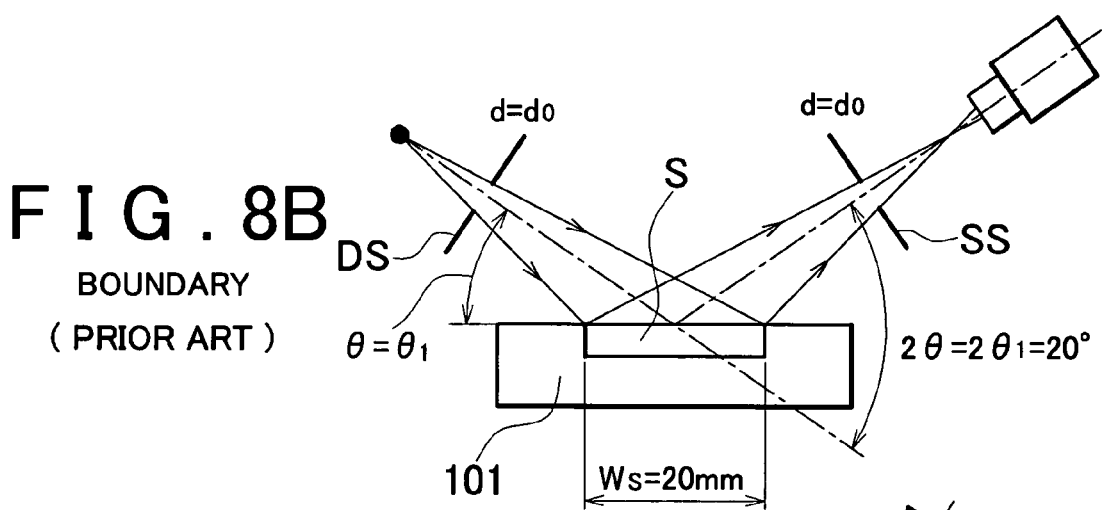
Figure 8C:
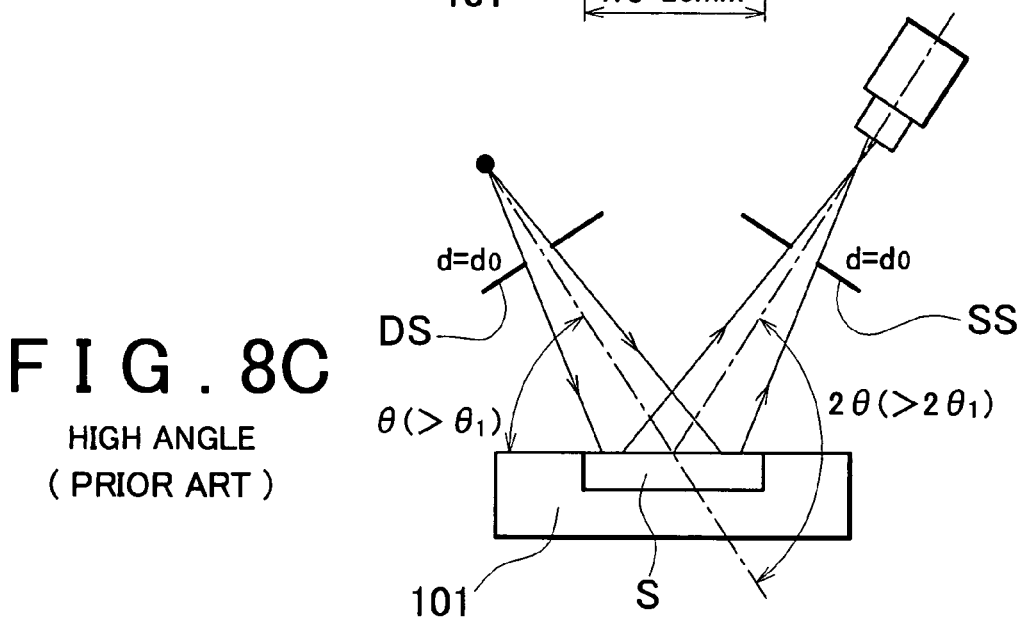
Figure 9A:
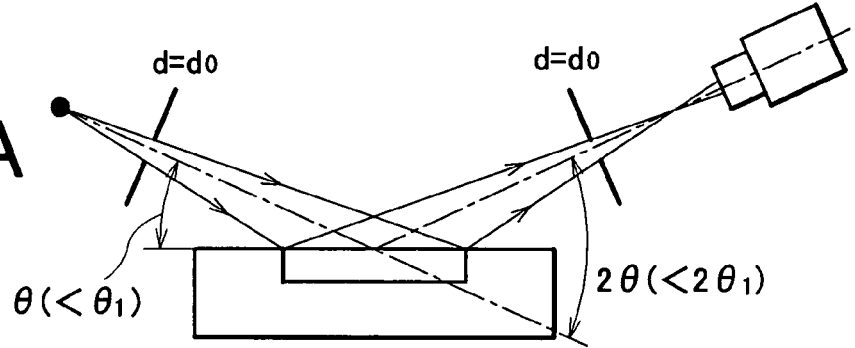
Figure 9B:
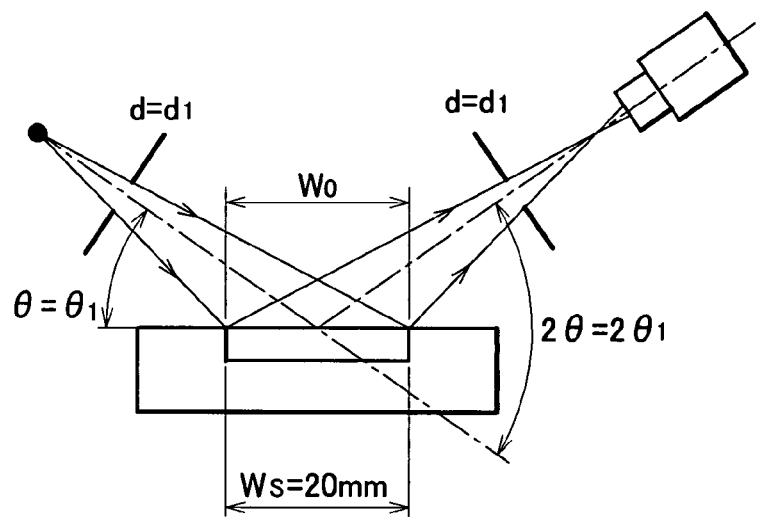
Figure 9C:
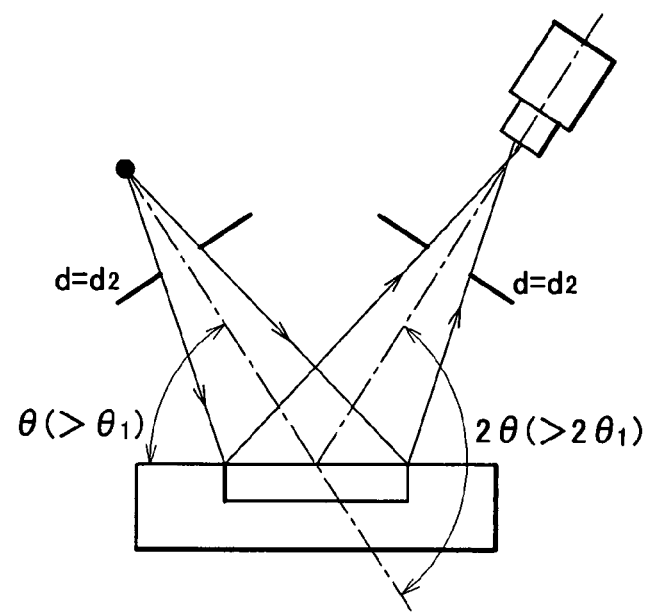
Figure 10:
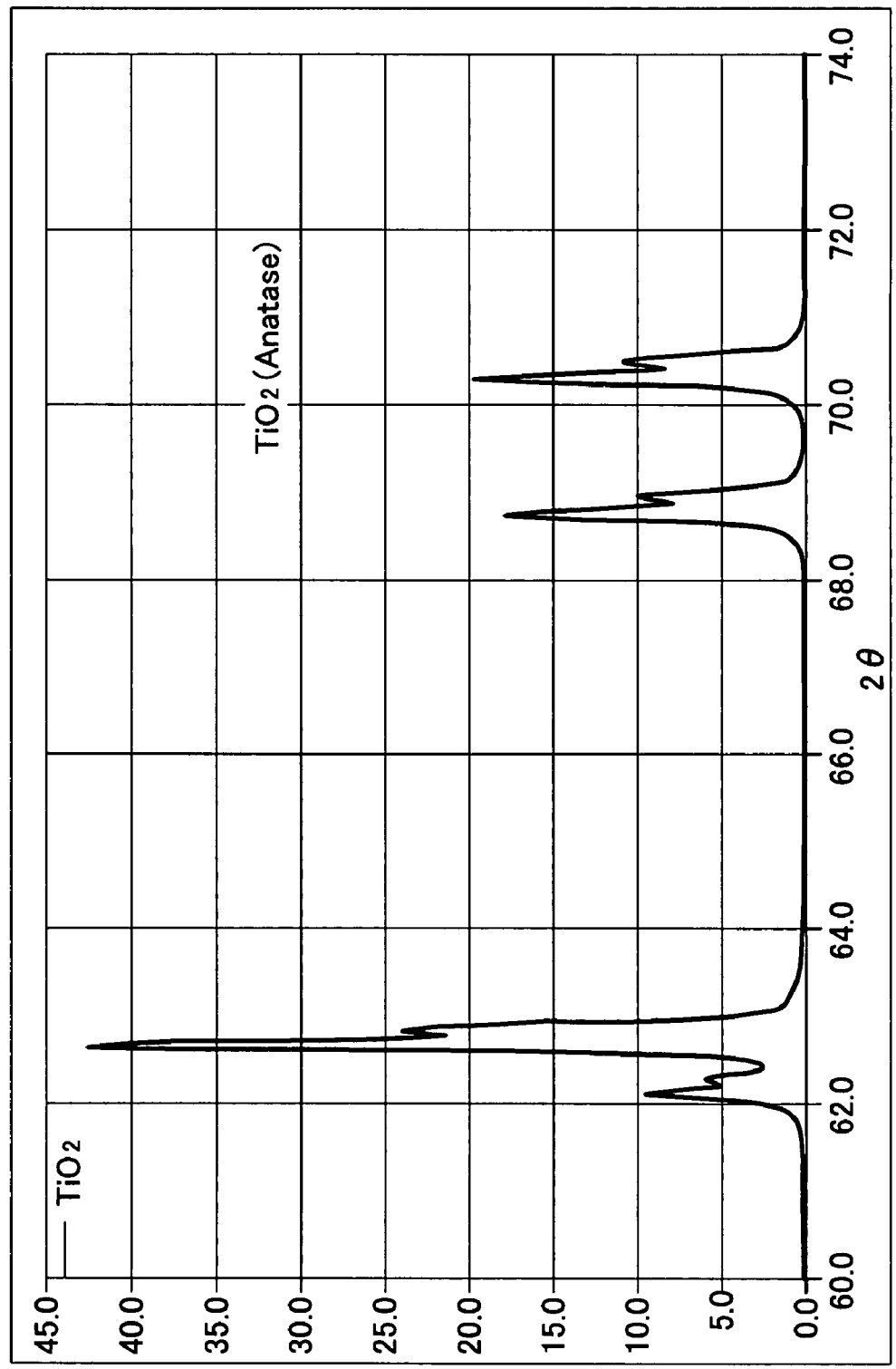
FIG. 10 is a graph showing a diffraction profile of a substance capable of being measured by an X-ray diffraction apparatus according to the present invention.
Figure 11:
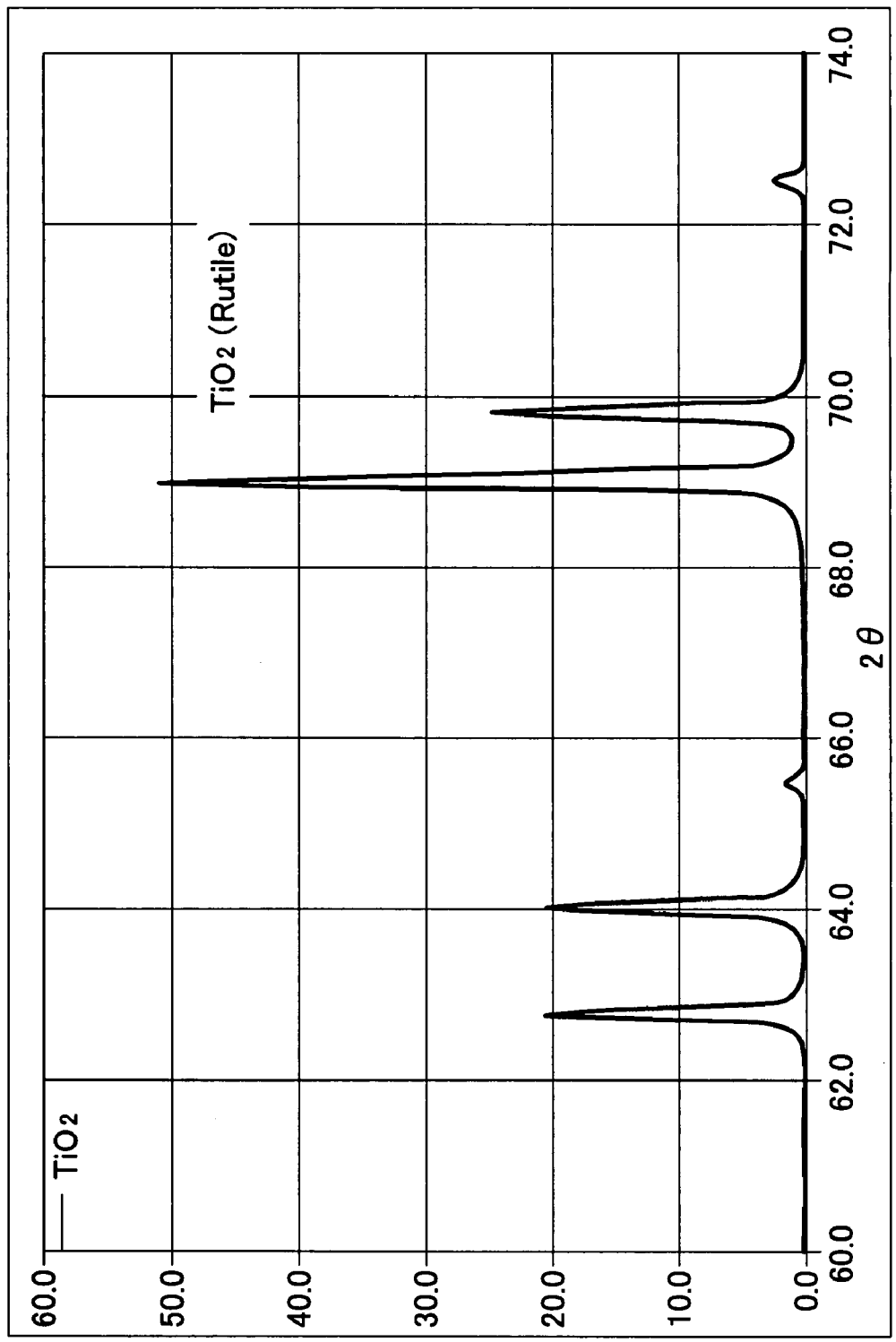
FIG. 11 is a graph showing a diffraction profile of another substance capable of being measured by an X-ray diffraction apparatus according to the present invention.
Figure 12:
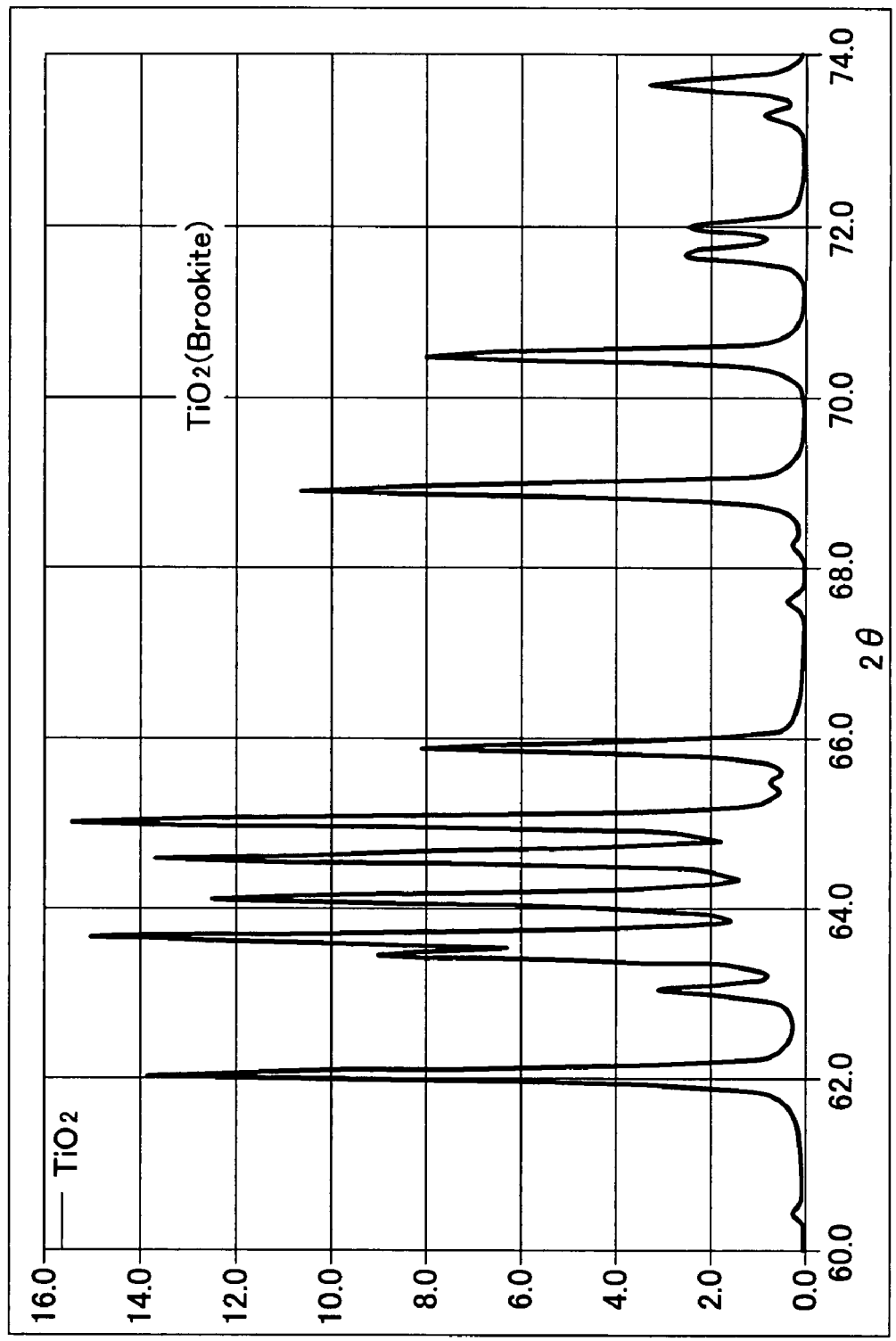
FIG. 12 is a graph showing a diffraction profile of still another substance capable of being measured by an X-ray diffraction apparatus according to the present invention.

In the case of the fixed-divergence angle method, the irradiation field of X-ray passed through the divergence slit DS and irradiated on the sample S in the low angle region (<$\theta_1$) shown in FIG. 8A is larger than the sample width $W_s$, thus increasing the background level. On the other hand, in the case of the present embodiment shown in FIG. 2A, the X-ray irradiation field of the divergence slit 2 is controlled to always coincide with the sample width $W_s$ in the low angle region, thus reducing the background level. Therefore, as shown by the curve B in FIG. 5, the value obtained when the background in the conventional fixed divergence angle method is set as a denominator and background in the method according to the present invention is set as a numerator becomes below "1" as the diffraction angle $2\theta$ becomes small. As a result, a value obtained when the P/B ratio in the conventional fixed divergence angle method is set as a denominator and P/B ratio in the method according to the present invention is set as a numerator becomes, as shown by the curve P/B, higher toward the low angle side in terms of the diffraction angle $2\theta$. That is, the P/B ratio in the low angle region obtained in the present embodiment is significantly improved to that obtained in the conventional fixed-divergence angle method.

ANOTHER EMBODIMENT

Although the present invention has been described in its preferred embodiment, it should be understood that the present invention is not limited to the specific embodiment and that various design changes may be made without departing from the scope of the present invention described in the claims.

Figure 6:
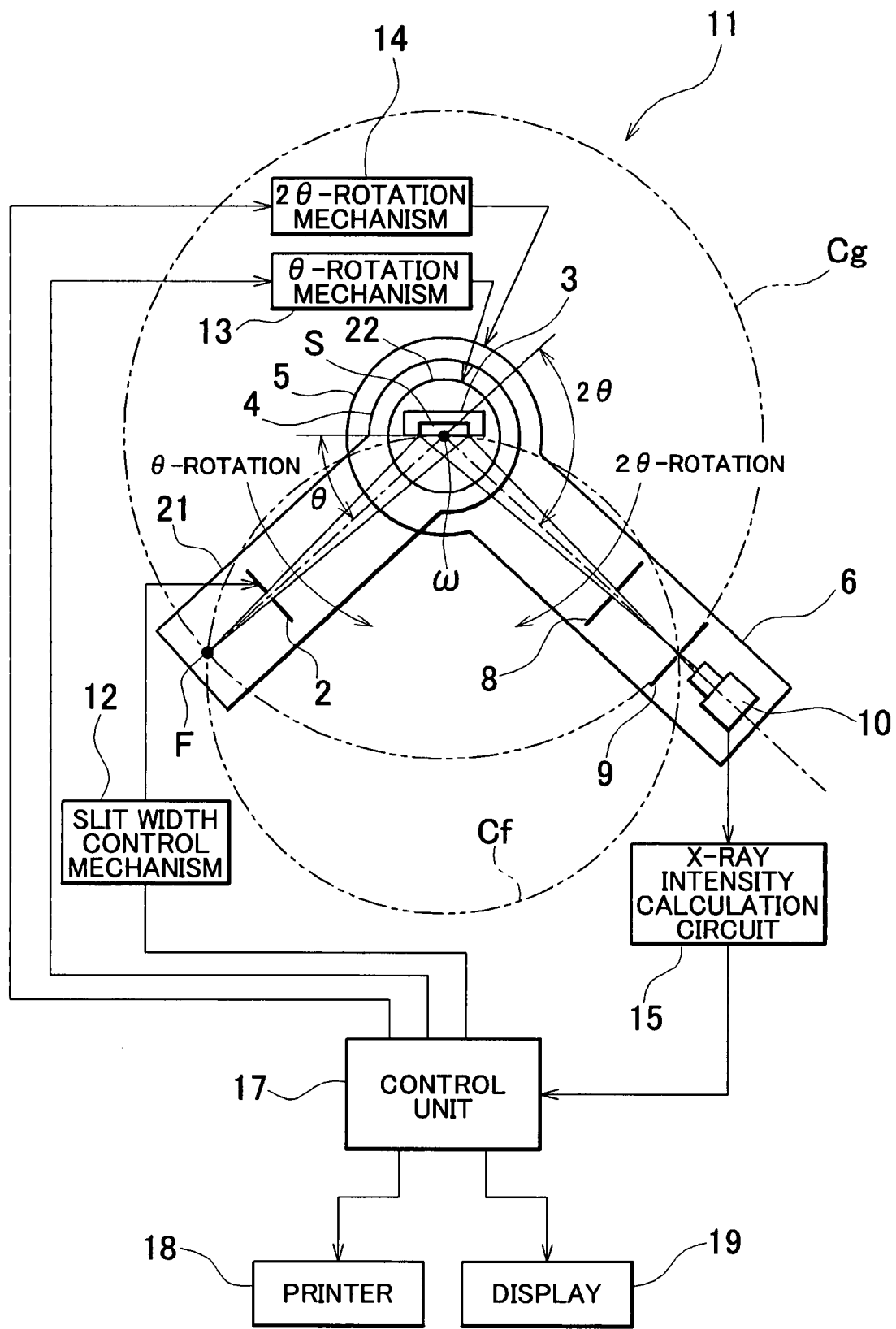
FIG. 6 is a plan view showing another embodiment of the X-ray diffraction apparatus according to the present invention.
Figure 7:
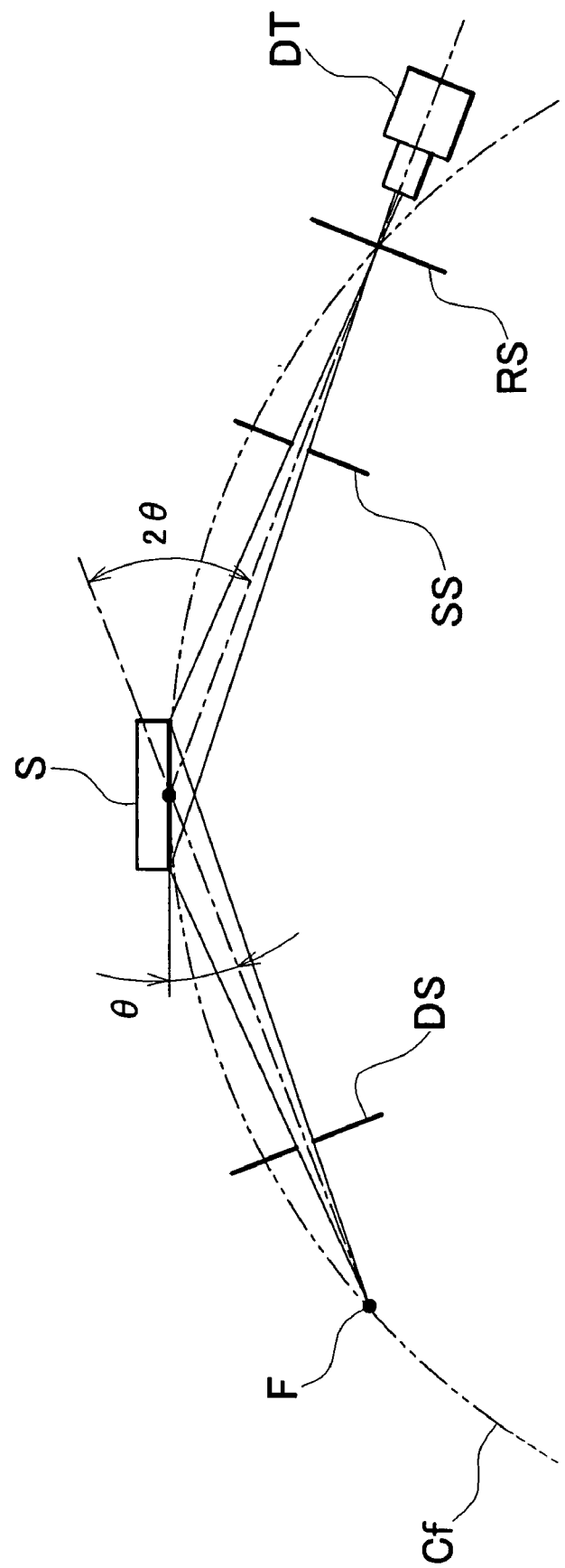
FIG. 7 is a view showing an example of a conventional X-ray diffraction apparatus.

In the embodiment shown in FIG. 1, the present invention is applied to a $\theta$-$2\theta$ optical system having a configuration in which the X-ray detector 10 is $2\theta$-rotated in the same direction as $\theta$-rotation at an angular speed double that of $\theta$-rotation. In place of this, the present invention may be applied to an X-ray diffraction apparatus 11 using a $\theta$-$2\theta$ rotation system shown in FIG. 6. In the rotation system shown in FIG. 6, the sample S is fixed to a sample stage 22, the X-ray source F and the divergence slit 2 are fixed on a X-ray source arm 21 extending from the $\theta$-rotation table 4, and the scattering slit 8, the receiving slit 9, the X-ray detector 10 are fixed on the detector arm 6 extending from the $2\theta$-rotation table 5. In this configuration, the X-ray source arm 21 and the detector arm 6 are rotated, in a synchronized manner, in the opposite directions by the same angle $\theta$ to thereby retain the positional relationship between the incident X-ray and X-ray detector 10 in terms of the incident angle $\theta$ and diffraction angle $2\theta$.

What is claimed is:

1. An X-ray diffraction apparatus comprising:
   an X-ray source which generates X-ray to be irradiated on a sample;
   an X-ray detector which detects X-ray emitted from the sample;
   a divergence slit which is disposed between the X-ray source and the sample, the slit width of which can be controlled;
   a scattering slit which is disposed between the sample and the X-ray detector, the slit width of which is constant;
   a $\theta$-rotator which changes the incident angle ($\theta$) of X-ray emitted from the X-ray source and entering the sample through the divergence slit;

a 2θ-rotator which changes the diffracted X-ray detection angle (2θ) at which the X-ray detector detects X-ray diffracted by the sample and passed through the scattering slit; and a divergence slit width controller which controls the slit width of the divergence slit, wherein the X-ray incident angle (θ) is changed by the θ-rotator, the diffracted X-ray detection angle (2θ) is changed by the 2θ-rotator such that the diffracted X-ray detection angle (2θ) at which the X-ray detector detects X-ray is kept at an angle double that of the X-ray incident angle (θ);

the slit width of the divergence slit is controlled by the divergence slit width controller such that the irradiation width of X-ray to be irradiated on the sample is made constant during a change in the X-ray incident angle (θ), the slit width of the scattering slit is kept constant, and X-ray emitted from the sample is detected by the X-ray detector.

2. The X-ray diffraction apparatus according to claim 1, wherein the divergence slit controller controls the slit width of the divergence slit such that the irradiation width of X-ray on the sample surface coincides with the sample width of the sample.

3. The X-ray diffraction apparatus according to claim 1, wherein the slit width of the scattering slit is constant at the point where the divergence angle is (½)°, 1°, or 2°.

4. The X-ray diffraction apparatus according to claim 1, wherein the slit width of the scattering slit is constant at the point where the divergence angle is (½)°, 1°, or 2°, and when the angle (2θ) of the scattering slit relative to X-ray entering the sample falls within a range of 10° to 40°, the X-ray width on the sample which is defined by the slit width of the scattering slit coincides with the sample width of the sample.

5. The X-ray diffraction apparatus according to claim 2, wherein the slit width of the scattering slit is constant at the point where the divergence angle is (½)°, 1°, or 2°.

6. The X-ray diffraction apparatus according to claim 2, wherein the slit width of the scattering slit is constant at the point where the divergence angle is (½)°, 1°, or 2°, and when the angle (2θ) of the scattering slit relative to X-ray entering the sample falls within a range of 10° to 40°, the X-ray width on the sample which is defined by the slit width of the scattering slit coincides with the sample width of the sample.

* * * * *